(12) United States Patent
Zhang et al.

(10) Patent No.: US 11,465,886 B2
(45) Date of Patent: Oct. 11, 2022

(54) SUSPENSION RAIL TYPE GREENHOUSE COMPREHENSIVE INFORMATION AUTOMATIC CRUISE MONITORING DEVICE

(71) Applicant: JIANGSU UNIVERSITY, Jiangsu (CN)

(72) Inventors: Xiaodong Zhang, Jiangsu (CN); Hanping Mao, Jiangsu (CN); Hongyan Gao, Jiangsu (CN); Zhiyu Zuo, Jiangsu (CN); Yixue Zhang, Jiangsu (CN)

(73) Assignee: JIANGSU UNIVERSITY

( * ) Notice: Subject to any disclaimer, the term of this patent is extended or adjusted under 35 U.S.C. 154(b) by 261 days.

(21) Appl. No.: 16/645,891

(22) PCT Filed: Nov. 16, 2018

(86) PCT No.: PCT/CN2018/115817
§ 371 (c)(1),
(2) Date: Mar. 10, 2020

(87) PCT Pub. No.: WO2019/134454
PCT Pub. Date: Jul. 11, 2019

(65) Prior Publication Data
US 2020/0325005 A1    Oct. 15, 2020

(30) Foreign Application Priority Data
Jan. 3, 2018    (CN) .......................... 201810004680.2

(51) Int. Cl.
*B66C 17/06*    (2006.01)
*G01B 11/06*    (2006.01)
(Continued)

(52) U.S. Cl.
CPC .......... *B66C 17/06* (2013.01); *G01B 11/0608* (2013.01); *G01D 5/26* (2013.01);
(Continued)

(58) Field of Classification Search
CPC ... B66C 17/06; G01B 11/0608; G01B 11/046; G01B 11/24; G01D 5/26; G01D 21/02;
(Continued)

(56) References Cited

U.S. PATENT DOCUMENTS 3,186,493 A    6/1965  Barry .............................. 172/26
RE31,023 E    9/1982  Hall, III ......................... 47/1 R
(Continued)

FOREIGN PATENT DOCUMENTS

CN    102017938    4/2011    ............. A01M 7/00
CN    102384767    3/2012    ............. G01D 21/02
(Continued)

OTHER PUBLICATIONS

Notice of Allowance issued U.S. Appl. No. 16/646,034, dated Apr. 29, 2022, 25 pages.
(Continued)

*Primary Examiner* — Mohamed K Amara
(74) *Attorney, Agent, or Firm* — Hayes Soloway P.C.

(57) ABSTRACT

A suspension rail type greenhouse comprehensive information automatic cruise monitoring device, includes a sliding rail a sliding platform, and a lifting and lowering mechanism suspended on a greenhouse truss; a multi-sensor system which includes a binocular vision multifunctional camera, a laser ranging sensor, an infrared temperature measuring sensor, an illumination intensity sensor, and a temperature and humidity sensor, and an electronically controlled rotary pan-tilt mounted below the lifting and lowering mechanism of the sliding platform; a detection azimuth overlooks plant canopies; and a multi-sensor system configured to perform stationary point detection on the plant canopies one by one along planting lines of plants under the driving of the sliding platform.

10 Claims, 6 Drawing Sheets

(51) Int. Cl.
*G01D 5/26* (2006.01)
*G01J 1/00* (2006.01)
*G01J 5/00* (2022.01)
*G01N 33/00* (2006.01)
*G05B 19/042* (2006.01)

(52) U.S. Cl.
CPC . *G01J 1/00* (2013.01); *G01J 5/00* (2013.01); *G01N 33/0098* (2013.01); *G05B 19/0428* (2013.01); *G05B 2219/2612* (2013.01)

(58) Field of Classification Search
CPC .... G01J 1/00; G01J 5/00; G01J 1/4204; G01J 5/0003; G01J 2005/0077; G01N 33/0098; G01N 21/359; G01N 2021/8466; G01N 21/6456; G01N 2021/3155; G01N 21/3554; G01N 33/025; G01N 27/223; G01N 21/64; G05B 19/0428; G05B 2219/2612; G05B 2219/37009; F16M 11/043; F16M 2200/061; F16M 11/18; F16M 11/24; A01G 9/249; A01G 25/09; G06T 2207/30188; G06T 7/11; G06T 7/0004; G06T 2207/10036; G06T 2207/10012; G06T 2207/10048; G06T 7/143; G06T 7/0002; G06T 2207/30108; G06T 2200/04; G06T 2207/10021; G06T 7/00; A01C 7/105
See application file for complete search history.

(56) References Cited

U.S. PATENT DOCUMENTS

| | | | |
|---|---|---|---|
| 4,612,996 A | 9/1986 | Wolf et al. | 172/26 J |
| 10,172,304 B2 | 1/2019 | Ayers et al. | A01G 33/00 |
| 10,597,896 B1 | 3/2020 | Hamilton et al. | E04H 15/10 |
| 11,287,411 B2 | 3/2022 | Miresmailli et al. | G01N 33/0098 |
| 2015/0015697 A1 | 1/2015 | Redden | |
| 2021/0149406 A1* | 5/2021 | Javault | A01D 45/26 |

FOREIGN PATENT DOCUMENTS

| | | | | |
|---|---|---|---|---|
| CN | 102721651 | | 10/2012 | G01N 21/25 |
| CN | 202773632 | | 3/2013 | A01G 31/02 |
| CN | 103264730 | | 8/2013 | B62D 55/06 |
| CN | 103439264 A | * | 12/2013 | G01N 21/25 |
| CN | 103488173 | | 1/2014 | G05D 1/02 |
| CN | 103699095 | | 4/2014 | G05B 19/418 |
| CN | 105825177 | | 8/2016 | G06K 9/00 |
| CN | 106323182 | | 1/2017 | G01B 11/08 |
| CN | 106406178 | | 2/2017 | G05B 19/042 |
| CN | 106441442 | | 2/2017 | G01D 21/02 |
| CN | 106687877 A | * | 5/2017 | A01B 69/001 |
| CN | 106989776 A | * | 7/2017 | G01D 21/02 |
| CN | 107486834 | | 12/2017 | B25J 5/02 |
| CN | 108362323 | | 8/2018 | G01D 21/02 |
| CN | 108387262 | | 8/2018 | G01D 21/02 |
| CN | 112710663 A | * | 4/2021 | G01N 21/84 |
| EP | 0 084 289 | | 6/1986 | A01G 9/24 |

OTHER PUBLICATIONS

International Search Report and Written Opinion issued in PCT/CN18/115817, dated Jan. 31, 2019, with English translation, 10 pgs.
International Search Report and Written Opinion issued in PCT/CN18/115816, dated Jan. 30, 2019, with English translation, 14 pgs.
Wang, et al., An Efficient and Labor Saving Pesticide Application Device and Method for Greenhouse, Greenhouse intelligent equipment series 33, Beijing Agricultural Intelligent Equipment Technology Research Center, Greenhouse & Horticulture, pp. 26-27, 2011. (with Machine translation).

* cited by examiner

SUSPENSION RAIL TYPE GREENHOUSE COMPREHENSIVE INFORMATION AUTOMATIC CRUISE MONITORING DEVICE

I. TECHNICAL FIELD

The present invention belongs to the field of intelligent agricultural machinery, and relates to a suspension rail-type greenhouse comprehensive information automatic cruise monitoring device.

II. BACKGROUND ART

Presently, Chinese greenhouse planting area. and yield are at the forefront in the world. However, most of the greenhouses in China still adopt the traditional planting irrigation model with large amount of water and fertilizer, which can't meet the demand of the crops owing to its blindness, and results in problems, such as low yield and quality of the crops, serious waste of resources, poor economic benefits. One of the main reasons is the lack of scientific management of the facilities and production; besides, it is difficult to obtain comprehensive information on the greenhouse crops and environment online and in real time to realize optimized regulation and control of water, fertilizer and environment on the basis of the actual demand of the crops and realize early warning against pests and diseases. In the past, manual and chemical methods are usually used for identification and detection of crop nutrition, growth and pests and diseases, which not only have low detection efficiency but also involve misjudgements, and might cause irreversible damages to crops. Owing to the unstructured environment of greenhouse planting and production, there are few advanced and applicable automatic monitoring equipment and methods for comprehensive information on greenhouse environment and crops that meet the actual production demands at present. The present invention employs a suspended rail-type detection platform to monitor plant growth and environment information automatically. The detection platform operates in an autonomous cruising mode and utilizes a multi-sensor detection system to collect comprehensive information on crop nutrition, growth, pests and diseases, and environment in a greenhouse. Compared with traditional methods and distributed detection methods, the method provided in the present invention greatly improves the accuracy of detection and identification, reduces the cost, and improves the operating efficiency.

The invention patent application No. CN201010519848.7 has disclosed a suspended self-propelled target spraying system, which comprises a guide rail, a self-propelled mobile platform, a Hall sensor, a spraying mechanical arm device, a binocular vision system, and a. PLC logic controller, etc., wherein the guide rail is mounted on the greenhouse ceiling and the spraying mechanical arm is mounted on the self-propelled mobile platform. Therefore, pesticides can be sprayed automatically in the greenhouse environment to avoid physical injuries to the operators during the pesticide spraying process and the efficiency is improved. However, the device lacks a greenhouse environment information detection function, and doesn't take consideration of the environmental factors of the greenhouse adequately.

Ma Wei, et al. of Beijing Agricultural Intelligent Equipment Research institute have developed a rail-type labor-saving operating apparatus for greenhouse. By connecting an installation rail to the structure of a greenhouse, the apparatus can be pushed by hand to travel smoothly with a mobile device, and all pesticide application and pressure boosting devices can be carried by the suspended platform. The apparatus solves the problems of large-area pesticide application to foe greenhouse crops and inconvenience in transportation, and alleviates the labor intensity. However, it still requires certain manual operation, and its automation level is not high enough.

The invention patent application No, CN201310192634.7 has disclosed a tracked robot mobile platform, wherein a control module controls driving wheel train and driven wheel train to drive the car body to travel according to data signals from a monitoring module. As the tracks, wheel trains, and car body of the tracked robot all adopt rigid connections, the bumps on an uneven road, which may cause damages to the detecting equipment mounted on the mobile platform and affect the stability of detection, cannot be filtered out.

The invention patent application No. CN201010519848.7 has disclosed a suspended self-propelled target spraying system, which comprises a guide rail, a self-propelled mobile platform, a Hall sensor, a spraying mechanical arm device, a binocular vision system, and a PLC logic controller, etc., wherein the guide rail is mounted on the greenhouse ceiling and the spraying mechanical arm is mounted on the self-propelled mobile platform. Therefore, pesticides can be sprayed automatically in the greenhouse environment to avoid physical injuries to the operators during the pesticide spraying process and the efficiency is improved. However, the device lacks a greenhouse environment information detection function, and doesn't take consideration of the environmental factors of the greenhouse adequately.

The invention patent application No. CN201310408112.6 has disclosed a multi-terrain intelligent mobile platform far detection, which comprises an autonomously travelling four-wheel carriage system and a four-axis rotor flight system, wherein the two systems are connected via a locking system and communicate with a PC terminal through a ZigBee wireless transmission network. The autonomously travelling four-wheel carriage system utilizes Arduino to control vehicle-mounted multi-parameter sensor module and driving module, etc.; the four-axis rotor flight system utilizes Arduino to control airborne multi-parameter sensor module and high-speed driving module, etc. When the platform encounters an insurmountable obstacle, the locking system can unlock automatically and thereby trigger the operation of the four-axis rotor flight system. The overall stability of the multi-terrain hybrid intelligent mobile platform is inferior to that of a mobile platform with an independent suspension system, whether it operates in a four-wheel mode or a flight mode. To operate in the flight mode, the mass of the airborne detecting equipment must be evenly distributed, and there is a limit to the weight of the airborne detecting equipment. Compared with single-mode mobile platforms, the multi-terrain hybrid intelligent mobile platform has a complex structure and a higher price.

In summary, as the existing intelligent mobile platforms are oriented to different task objectives, these platforms and the corresponding methods can't meet the requirements of greenhouse plant growth and environment information detection equipment for the detection accuracy and stability of a platform in unstructured greenhouse environments. It is difficult to realize automatic cruise detection of nutrition, growth, pest and disease information of crops in different growing stages, of different types, and in different plant sizes (small, medium and large) with existing intelligent mobile platforms and methods.

III. CONTENTS OF THE INVENTION

In view of the drawbacks in the prior art, the object of the present invention is to provide a suspended rail-type automatic cruise monitoring device for comprehensive greenhouse information, to realize synchronous automatic cruise monitoring of nutrition, water, growth, and pest and disease information of crops, and environmental lighting and temperature and humidity information in a greenhouse.

To attain the object described above, the present invention employs the following technical scheme:

A suspended rail-type automatic cruise monitoring device for comprehensive greenhouse information, comprising a rail assembly, a travelling mechanism, a sliding platform, a multi-sensor system, and a control cabinet assembly, wherein, The rail assembly mainly comprises a slide rail and a toothed rack that are fixed to a structural cross-beam of the greenhouse respectively;

The travelling mechanism comprises a gear rack A, a gear rack B, a deceleration motor, a gear shaft, gears, a bearing, and a photoelectric encoder, wherein the deceleration motor is connected to one end of the gear shaft by a spline; the gears are fixed on the gear shaft and mesh with the toothed rack, the other end of the gear shaft is mounted on the bearing, and the bearing is connected to the gear rack A by bolts; the gear rack A is connected to the gear rack B by bolts; top threads of the shaft of the photoelectric encoder are connected with the gear shaft to realize calculation and detection of travelling distance and position;

The sliding platform is mainly composed of a lifting mechanism and an electronically-controlled rotating head. It comprises four sets of pulleys, a terminal limit switch, a suspension, a lifting mechanism, an electronically-controlled rotating head, a power supply of the lifting mechanism, and a DSP (Digital Signal Processor) movement controller. The pulleys are fixed to the suspension and mounted in the slide channel of the slide rail, the suspension is fixed to the top of the lifting mechanism, the terminal limit switch is fixed to the top of the suspension at two end positions in the forward/backward travelling direction, the bottom of the lifting mechanism is fixed to the electronically-controlled rotating head, and the DSP movement controller is used to control the forward and backward movement of the sliding platform and the up and down movement of the lifting mechanism; the power supply of the lifting mechanism supplies power to the sliding platform;

The multi-sensor system comprises a light intensity sensor, a laser ranging sensor, an infrared temperature measurement sensor, and temperature and humidity sensors, and a binocular multi-function imaging system, wherein, a sensor bracket A and a sensor bracket B are mounted on the two sides of the bottom end of the electronically-controlled rotating head respectively; the binocular multi-functional imaging system comprises a visible light multi-functional imaging system and a near-infrared multi-functional imaging system, and is fixed on the sensor bracket A, with the viewing fields facing downward; a set of front optical filters for visible light is mounted on the front end of the visible light multi-function imaging system, to acquire characteristic image information of crop nutrition; a set of front optical filters for near-infrared light is mounted on the front end of the near-infrared multi-functional imaging system, to acquire characteristic image information of water stress in the crops; besides, the visible light multi-functional imaging system and the near-infrared multi-functional imaging system can be used as multiplexing camera for binocular vision matching, to realize three-dimensional imaging and measurement of plant height and crown width area of the crops; the infrared temperature measurement sensor, the temperature and humidity sensor, the laser ranging sensor, and the light intensity sensor are fixed on the two sides of the sensor bracket B in an overlooking position, with a vertically downward detection direction;

The control cabinet portion comprises an industrial PC (Personal Computer) and a power supply of the industrial PC, wherein the industrial PC is connected with the photoelectric encoder, the DSP movement controller and the multi-sensor system.

Furthermore, the slide rail is fixed below a main suspension beam, and the toothed rack is fixed below an auxiliary suspension beam.

Furthermore, a cross brace is arranged between the main suspension beam and the auxiliary suspension beam.

Furthermore, the seam between the two adjacent sections of the main suspension beam and the auxiliary suspension beam is fastened by means of connecting plates.

Furthermore, the rail assembly consists of three portions: a left portion, a middle portion, and a right portion.

Furthermore, the lifting mechanism is a scissor-fork telescopic mechanism.

Furthermore, the set of optical filters for visible light comprises 556 nm, 472 nm and 680 nm optical filters.

Furthermore, the set of optical filters for near-infrared light comprises 930 nm and 1,420 nm optical filters.

Furthermore, the control cabinet portion further comprises a touch display screen and a power supply of the display screen, wherein the touch display screen is connected with the industrial PC.

Beneficial Effects of the Present Invention (1) In the automatic cruise monitoring device employed in the present invention, the multi-sensor detection system is suspended and mounted to a slide rail in the overhead space of the greenhouse; thus, the problem that a ground self-propelled automatic cruise detection platform is severely affected by the conditions of the road surface and planting environment under a dense planting condition in the greenhouse can be effectively overcome.

(2) In the automatic cruise monitoring device employed in the present invention, the sliding platform employs a lifting mechanism in combination with an electronically-controlled rotating head. Thus, not only accurate positioning in the travelling direction for detection can be realized, but also multi-sensor cruise detection in different detection distances, in different overlook viewing fields, and at different detection angles can be realized. Therefore, multi-sensor monitoring of large-size plants such as tomato and cucumber can be carried out; besides, by adjusting the detection distance and the azimuth angle of the head, the demand for detection of small-size crops (e.g., lettuce, etc.) and greenhouse crops in different growing stages (e.g., seedling stage, etc.) can be met.

(3) The multi-sensor system employed in the present invention uses a binocular vision multi-functional camera in combination with a laser ranging sensor and an infrared temperature detector, and thereby can realize online cruise monitoring of comprehensive information of greenhouse crops, including images and infrared temperature characteristics of plant nutrition, water, and pests and diseases, and characteristics of plant crown width, plant height, and fruit growth, etc., by means of multi-sensor information fusion.

(4) The suspended automatic cruise detection platform employed in the present invention can carry out on-line regular cruise monitoring for comprehensive information of crops and environment in the entire greenhouse, and provides a scientific basis for regulation and management of water, fertilizer, and environment in the greenhouse, and can greatly reduce the input of detecting equipment and personnel, effectively avoid operating errors by personnel, and improve the accuracy and efficiency of detection of environment and plant growth information in the greenhouse, when compared with traditional artificial experience and distributed monitoring systems.

(5) As a control system, the universal platform employed in the present invention has excellent transportability, can be further developed easily to extend the functions, and has good compatibility for the carried detecting equipment.

IV. DESCRIPTION OF DRAWINGS

Figure 1:
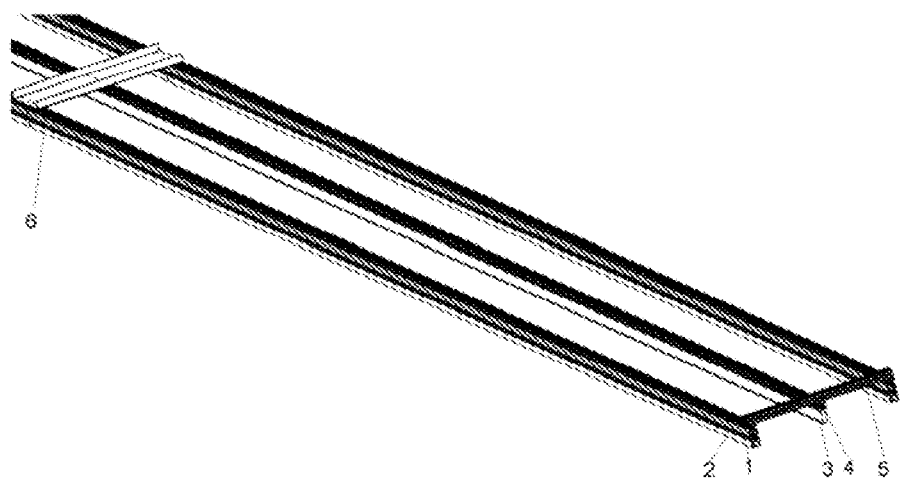
FIG. 1 is a schematic structural diagram of the rail assembly of the suspended rail-type automatic cruise monitoring device for comprehensive greenhouse information according to the present invention.

IN THE FIGURES 1-slide rail; 2-main suspension beam; 3-auxiliary suspension beam; 4-toothed rack; 5-cross brace; 6-rail connecting plate; 7-gear rack A; 8-gear rack B; 9-deceleration motor; 10-gear shaft; 11-gear; 12-bearing; 13-photoelectric encoder; 14-pulley; 15-DSP movement controller; 16-power supply of the lifting mechanism; 17-terminal limit switch; 18-suspension; 19-lifting mechanism; 20-lifting coiled strip; 21-electronically-controlled rotating head; 22-1-visible light multi-function imaging system; 22-2-near-infrared multi-function imaging system; 23-1-sensor bracket A; 23-2-sensor bracket B; 24-head bracket; 25-infrared temperature measurement sensor; 26-temperature and humidity sensor; 27-laser ranging sensor; 28-light intensity sensor; 29-control cabinet body; 30-touch display screen; 31-power supply of the display screen; 32-industrial PC; 33-power supply of the industrial PC; 34-power socket; 35-cultivation tank; 36-landmark sensor; 37-plant; 38-grid scanning trajectory of multi-sensor system

V. EMBODIMENTS

Hereunder the present invention will he further detailed in examples with reference to the accompanying drawings, but the protection scope of the present invention is not limited thereto.

The suspended rail-type automatic cruise monitoring device for comprehensive greenhouse information described in the present invention comprises a rail assembly; a travelling mechanism, a sliding platform, a multi-sensor system, and a control cabinet assembly.

As thou in FIG. 1, the track assembly mainly consists of sliding rails 1 and rack 4, respectively fixed on the cross structural beam of the greenhouse. Specifically, the left middle right three parts of the track assembly are composed; The sliding track 1 as fixed below the hanging main beam 2 and is the sliding track of the sliding platform and walking mechanism. The slip track 1 of the left and right parts is fixed on the left and right suspended main beams 2. The left and right suspended main beams 2 are parallel structures with an interval of 700 mm. The length of the left and right main beams is 18 meters, and they are respectively composed of 3 aluminum profiles with a length of 6 meters, 30×60. The left and right sliding track 1 has the same length of 18 meters and is composed of 3 stainless steel tracks 6 meters long respectively. The sliding track 1 length is tightly connected with the hanging main beam 2 every 500 mm through t-bolt and nut. In the parallel middle line with the suspension main beam 2, the suspension auxiliary beam 3 is installed, the suspension auxiliary beam 3 is composed of 3 30×30 aluminum profiles with a length of 6 meters, the bottom of which is fixed by T screw with rack 4, rack 4 is 18 meters long, and is composed of 6 rack fixed connections with a length of 3 meters.

In order to maintain straightness and structural stiffness between the suspended main beam 2 and the suspended auxiliary beam 3, in the direction of track length, the transverse brace 5 is used every 500 mm to tighten and connect the main beam 2 and the suspended auxiliary beam 3 through t-shaped bolts and nuts, so that the suspended main beam 2 and the suspended auxiliary beam 3 become an integral whole to ensure the structural stiffness. At the joints where the 6-meter profiles used for hanging main beam 2 and hanging auxiliary beam 3 are connected, the connecting plate 6 is used to tighten the connection between the suspended main beam 2 and the suspended auxiliary beam 3 through t-shaped bolts and nuts, so as to ensure the smooth transition of the sliding platform along the sliding track 1 at the joints.

Figure 2:
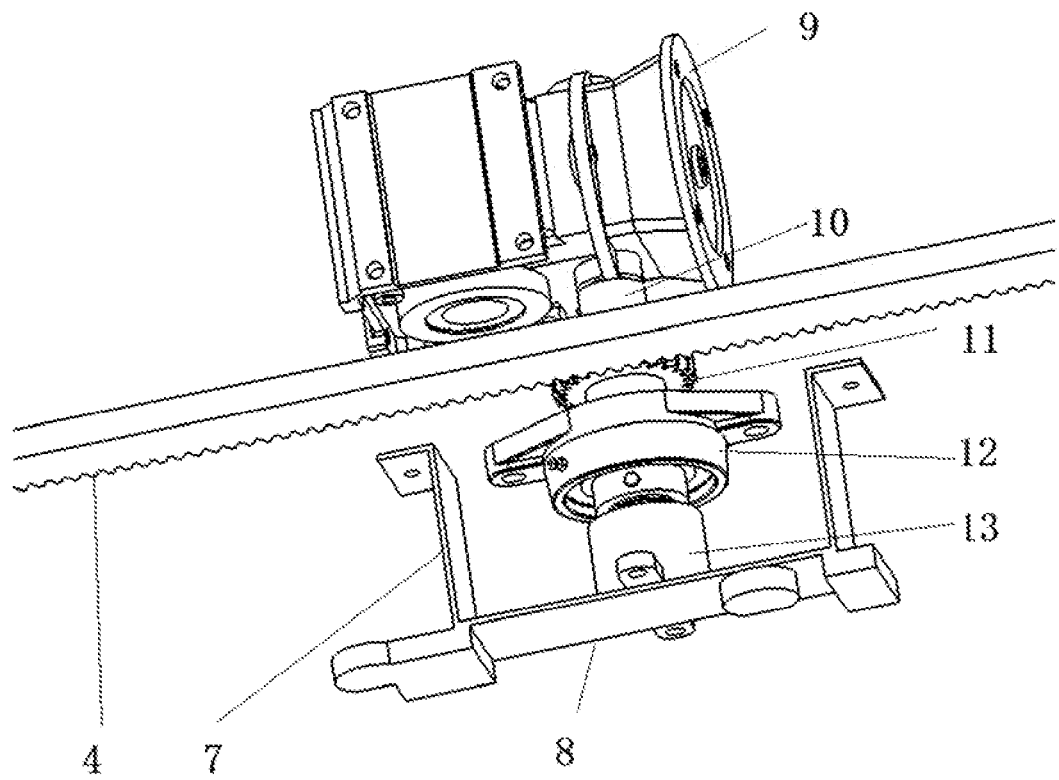
FIG. 2 is a schematic diagram of the travelling mechanism of the suspended rail-type automatic cruise monitoring device for comprehensive greenhouse information.

The walking mechanism is shown in FIG. 2. The walking mechanism is composed of rack 4, gear rack A7, gear rack B8, reduction motor 9, gear shaft 10, gear 11, bearing 12 and photoelectric encoder 13. The reduction motor 9 is connected with the gear shaft 10 through the spline on the shaft. Bearing 12 is connected to gear frame A7 through bolts and nuts. Gear rack A7 and gear rack A8 are connected by bolls and nuts; The photoelectric encoder 13 is connected to the gear shaft 10 through the top wire on the shaft to realize the calculation and detection of travel distance and position. The traveling mechanism is connected with the sliding track 1 and rack 4 of the track assembly to form a set of rack and pinion mechanism and a set of slide track mechanism.

Figure 3:
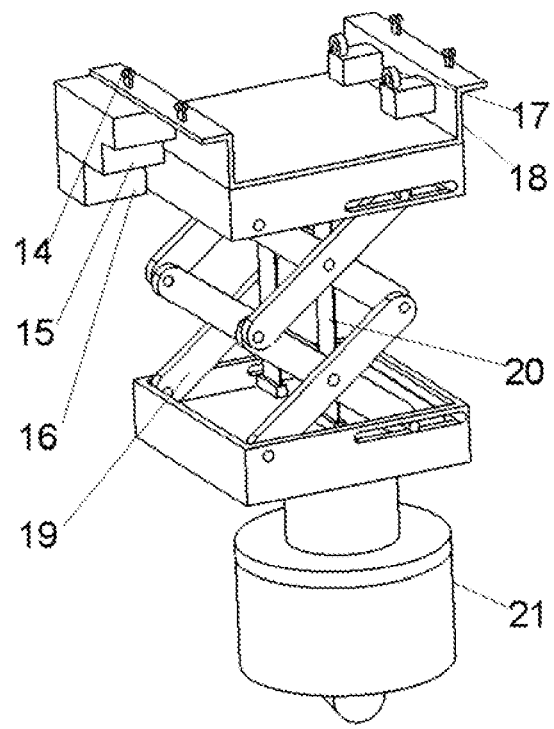
FIG. 3 is a schematic structural diagram of the sliding platform of the suspended rail-type automatic cruise monitoring device for comprehensive greenhouse information.

The main body of the sliding platform is driven by a walking mechanism, as shown in FIG. 3. The sliding platform is composed of 4 groups of pulleys 14, terminal limit switch 17, suspension 18, lifting mechanism 19, electrically controlled rotating head 21, lifting mechanism power 16 and DSP motion controller 15. Pulley 14 and suspension 18 are connected as a whole through bolts and suspended in the chute of slide rail 1, which can slide along the length direction of slide rail 1 as a whole with pulley 14. The lifting mechanism 19 and suspension 18 are fastened together with the base and suspension 18 by bolts and nuts; Lifting mechanism for the shear knife and fork telescopic mechanism, by controlling the lifting coil with 20 telescopic, to achieve the sliding platform lifting operation, in order to facilitate the multi-sensor system for the best height detection bit up and down adjustment. The terminal limit switch 17 of the front and rear moving directions is fixed on the top of the suspension 18 with t-screw along the two end positions of the front and rear moving directions. When the equipment runs to the end, the front end of the limit block touches the terminal limit switch 17 to make the whole system power off and brake.

Electrically controlled rotating cradle head 21 and the bottom of lifting mechanism 19 are connected by bolts and nuts; The lifting mechanism power supply 16, DSP motion controller 15, signal connection and other communication devices are fixed on the sliding platform and fixed on the moving direction end face of the lifting mechanism 19 by bolts and nuts. DSP motion controller 15 can realize the control of movement and lifting of the sliding platform before and after movement. The multi-sensor system in electrically controlled rotating cradle head 21 below, the multi-sensor system is driven by the electrically controlled rotating cradle head to implement level around 360° in the direction of rotation and the vertical direction of 180° rotating, lifting mechanism, under the drive control of DSP motion controller 15, can satisfy different detection range, overlooking the view, the different Angle of multi-sensor detecting demand.

Figure 4:
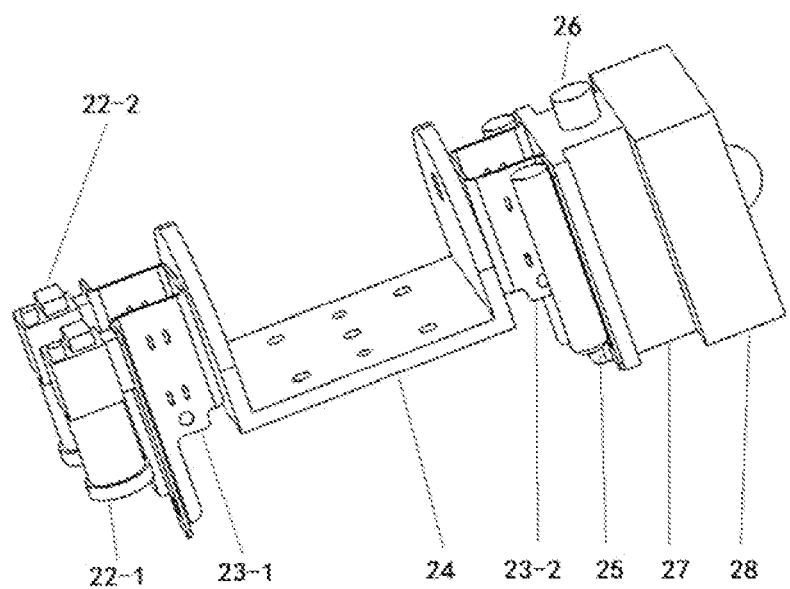
FIG. 4 is a schematic diagram of the multi-sensor system of the suspended rail-type automatic cruise monitoring device for comprehensive greenhouse information.
Figure 5:
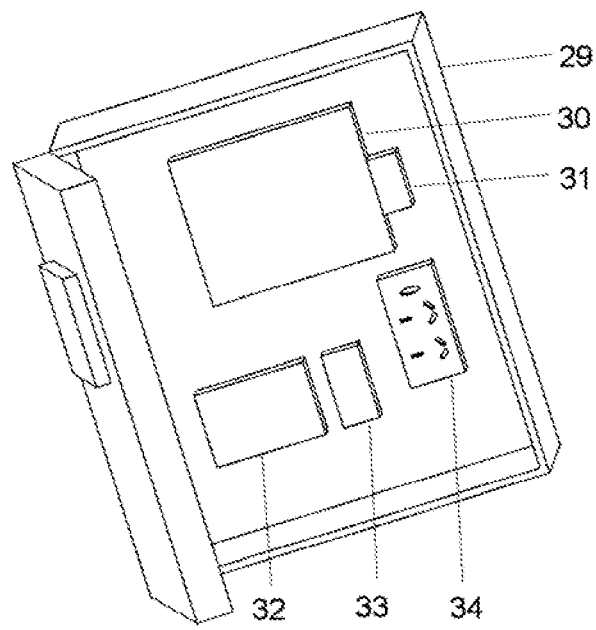
FIG. 5 is a schematic structural diagram of the control cabinet of the suspended rail-type automatic cruise monitoring device for comprehensive greenhouse information.
Figure 6:
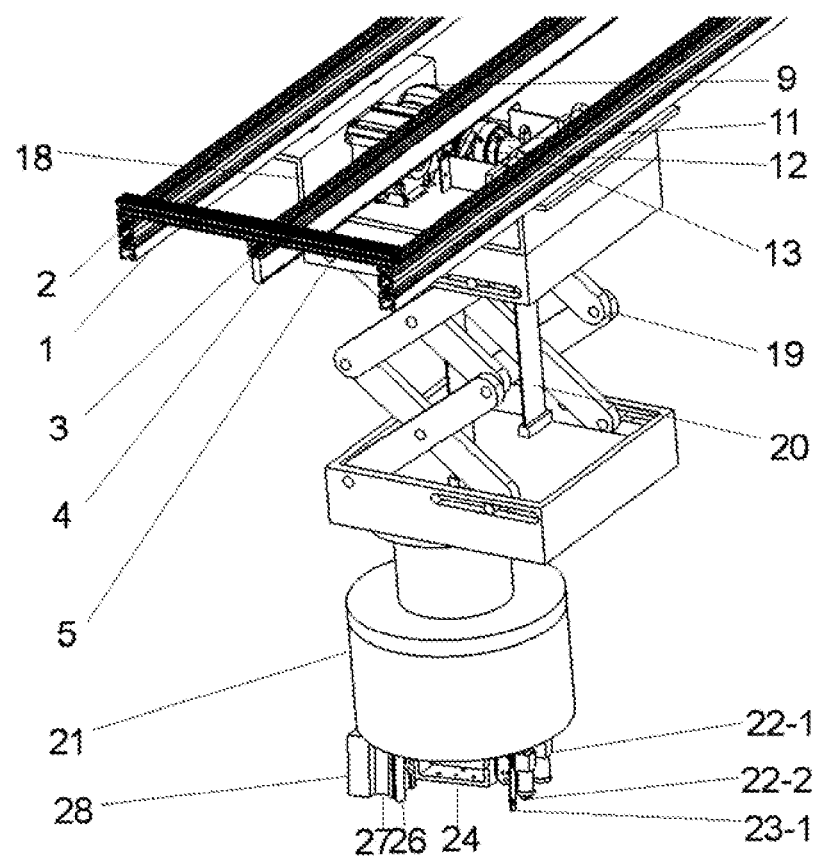
FIG. 6 is a schematic diagram of the overall structure of the suspended rail-type automatic cruise monitoring device for comprehensive greenhouse information.
Figure 7:
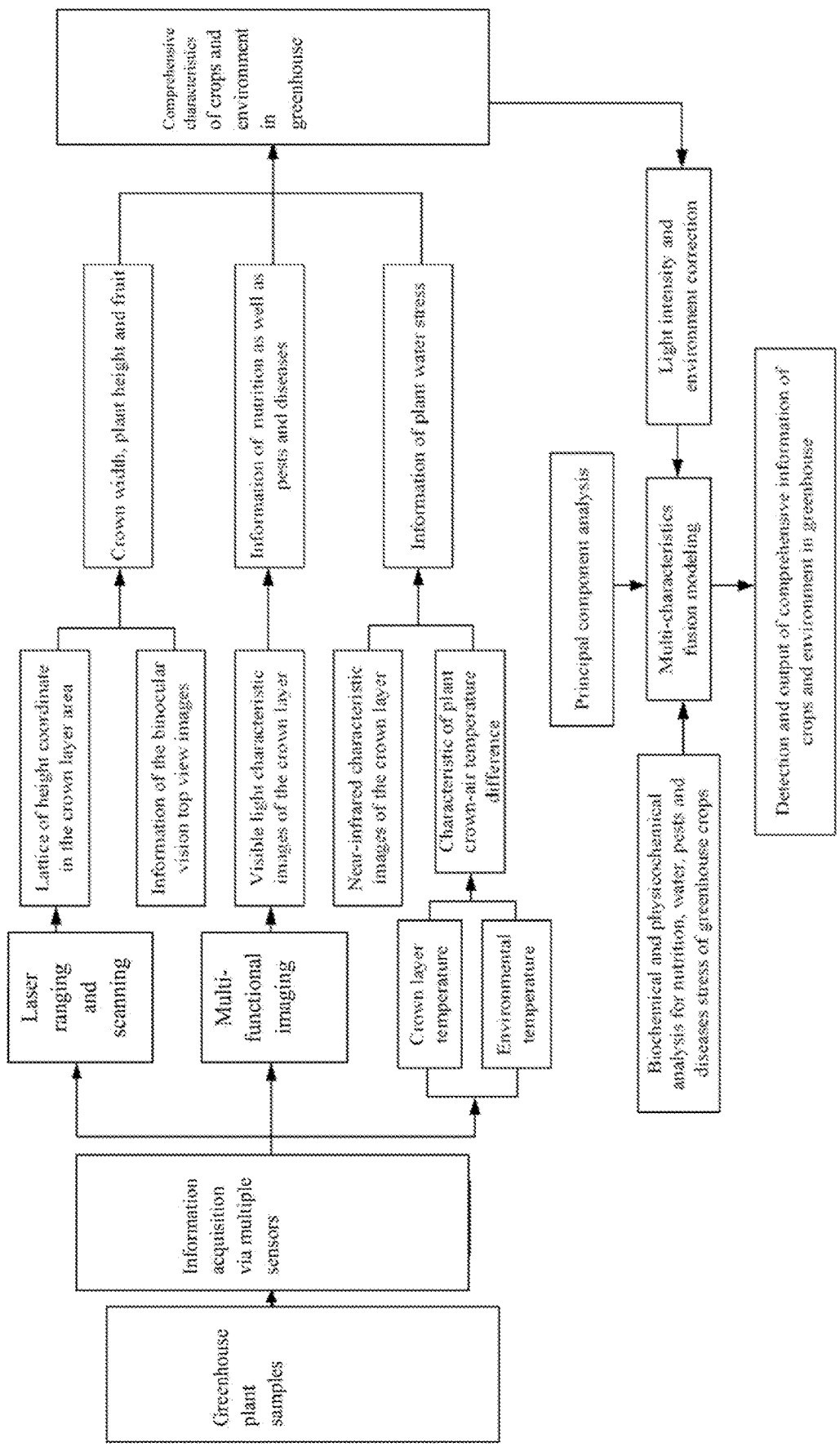
FIG. 7 is a flow chart of an greenhouse information automatic monitoring and multi-sensor detection method based on the suspended slide rail platform.
Figure 8:
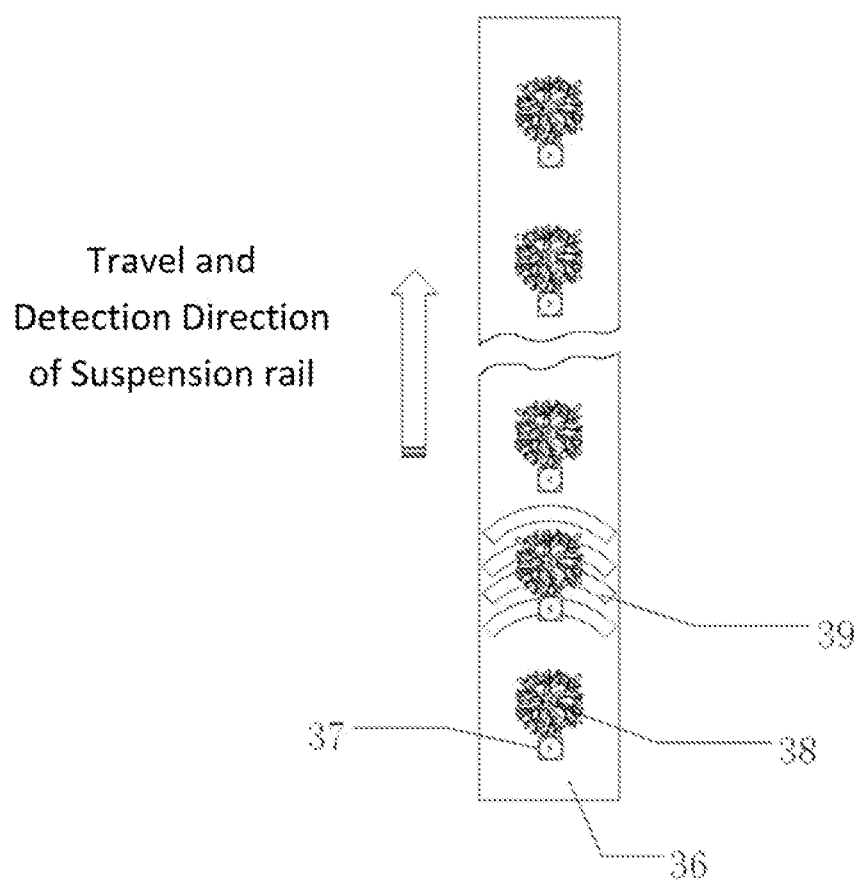
FIG. 8 is a schematic diagram of sensor grid scanning of the automatic greenhouse information monitoring method based on the suspended slide rail platform.
Figure 9:
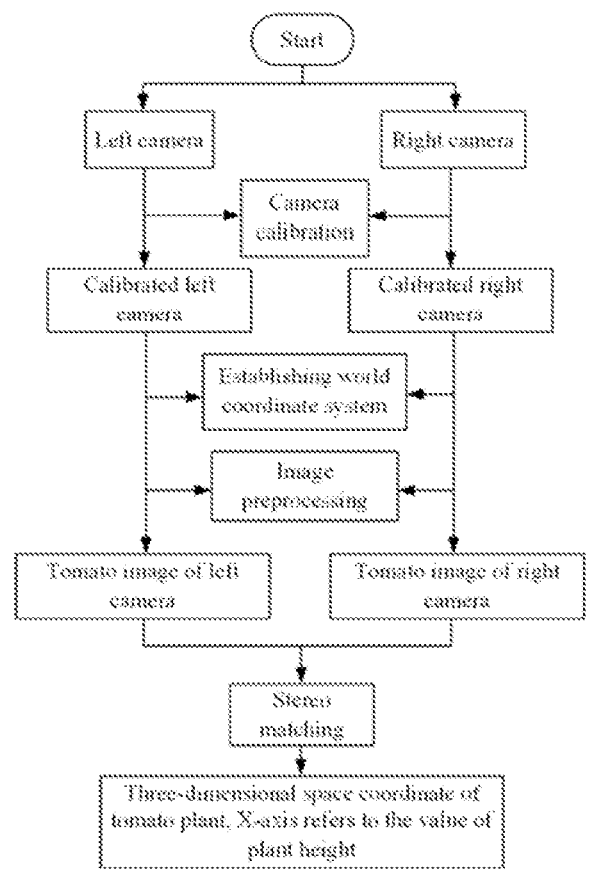
FIG. 9 shows the binocular 3D vision matching process of the automatic greenhouse information monitoring method based on the suspended slide rail platform.

As shown in FIG. 4, the multi-sensor system includes light intensity sensor 28, laser ranging sensor 27, infrared temperature sensor 25, temperature and humidity sensor 26, and binocular multi-function imaging system. Sensor bracket a23-1 and sensor bracket b23-2 are respectively installed on both sides of the cradle holder 24 at the lower end of the electrically controlled rotating cradle holder 21. The binocular multifunctional imaging system includes the visible light multifunctional imaging system 22-1 and the near-infrared multifunctional imaging system 22-2, which is fixed on the sensor bracket a23-1 with the field of view downward. The front end of the visible light multifunctional imaging system 224 is equipped with a set of pre-visible light filters including 556 nm, 472 nm and 680 nm fillers, which can achieve the acquisition of image information of crop nutrition characteristics. The front end of the nir multifunctional imaging system 22-2 is equipped with a group of front nir filters including 930 nm and 1420 nm filters, which can achieve the acquisition of characteristic image information of crop water stress. At the same time, visible light multifunctional imaging system 22-1 and near-infrared multifunctional imaging system 22-2 can be used as multiplexing cameras to perform binocular visual matching, achieve stereoscopic imaging, and achieve the measurement of plant height and crown width area. The infrared temperature sensor 25, temperature and humidity sensor 26, laser ranging sensor 27 and light intensity sensor 28 are fixed on both sides of the sensor bracket b23-2, with the top view position and the detection direction vertically downward.

The control cabinet is independently fixed at the front of the greenhouse. The control cabinet is connected to the walking mechanism, sliding platform and multi-sensor system respectively through 1394 data line for information interaction. The control cabinet provides power to the walking mechanism, sliding platform and multi-sensor system through the power cord. The control cabinet assembly comprises a touch display screen 30, a power supply of display screen 31, an industrial PC 32, a power supply of the industrial PC 33, a power socket 34 and a control cabinet body 29. The industrial PC 32 is connected with the photoelectric encoder 13, the DSP movement controller 15 and the multi-sensor system. The touch display screen 30 is fixed to the bottom of the control cabinet 29 via a base, the touch display screen 30 is connected with the industrial PC 32, and the industrial PC 32, the power supply of the industrial PC 33 and the power socket 34 are fixed to the bottom of the control cabinet body 29 by bolts and nuts.

When the suspended rail-type automatic cruise monitoring device for comprehensive greenhouse information is used for automatic cruise monitoring of comprehensive greenhouse information, it is operated according to the following steps:

Step 1. System Initialization:

Press the power button in the control cabinet to start the suspended rail-type monitoring system for comprehensive greenhouse information and let the system perform self-check, start the industrial PC 32, switch on the touch display screen 30, and start the DSP movement controller 15; return the sliding platform to zero position after the system is started, regardless of the current stopping position of the sliding platform.

Step 2. System Setting

1) Sample Setting and Sampling Interval Setting

As the system is applicable to different types of facilities and crops, the type, planting time and growing period of the crops must be set with the touch display screen 30 first. As the system uses a "plant-by-plant detection" working mode, it is necessary to set the plant spacing for the plants 37 to be detected in the cultivation tank 35 with the touch display screen 30 at first, and then set the landmark sensors 36, the movement interval of the sliding platform, and the sampling interval of the multi-sensor system, to obtain a grid scanning trajectory 38 of the multi-sensor system.

2) Detection Parameter Setting

Set the detection mode and detection parameters with the touch display screen 30, wherein, the detection modes include four modes: crop nutrition stress detection, pest and disease detection, water stress detection, and growth detection; wherein the parameter setting includes selection of parameters for detection of nitrogen, phosphorus and potassium in the nutrition stress mode, type identification in the pest and disease detection mode, and plant height, crown width, and fruits in the growth detection mode. The parameter selection and setting are based on the detection requirements and working efficiency of the present greenhouse operation;

3) Sliding Platform Movement Setting

After setting the detection mode and parameters, it is necessary to use the touch display screen 30 to set the movement journey of the sliding platform according to the detection objects and detection parameters. Different movement journey may be selected according to the detection parameters, and growing periods and types of the crops.

Lower detection positions may be selected for crops in a seedling stage or small-size crops (e.g., lettuce); higher detection positions may be selected for large-size crops (e.g., tomato and cucumber). The selection is based on a criterion that the crown layer area detected at the initial detection position shall account for more than 70% of the viewing field area and the distance from the plant top to the sensors shall be between 500 mm and 1,000 mm. If at criterion is not met, the imaging lens shall be replaced to meet the above-mentioned parameter requirements.

Step 3. Detection Process

After the setting process is completed, the system sends an instruction to the DSP movement controller 15 and the multi-sensor system via the industrial PC 32, to carry out movement control and execute a process for detecting crop nutrition, water, growth, and pest and disease information according to a preset detection procedure. According to the position instruction sent from the industrial PC 32, the DSP movement controller 15 sends a signal to the deceleration motor 9 first, the deceleration motor 9 drives the gear shaft 10 to rotate with the gear 11, the gear 11 is engaged with the toothed rack 4, and drives the entire sliding platform to sequentially move on the slide rail 1 by means of the pulleys 14 to a position above the crop; then, according to the preset positions and serial numbers of the landmark sensors 36, multi-sensor information detection is carried out for the crop in a point-by-point detection mode. The specific process is as follows:

1) Target Positioning of the Sliding Platform

According to the detection interval set in the sub-step 1) in the step 2, a landmark sensor 36 is laid in advance at the forefront of the plant at each detection position. After the sliding platform moves according to the preset journey and detects the landmark, the movement in the traveling direction stops. The industrial PC 32 sends an instruction to the DSP movement controller 15 to drive the lifting mechanism 19, so that the lifting mechanism of the sliding platform is lowered to a preset elevation; thus, the target positioning of the sliding platform is completed, multi-sensor information detection can he commenced at the target point;

2) Multi-Sensor Information Detection

After reaching a detection position sequentially, the industrial PC 32 sends a signal to the DSP movement controller 15 to drive the electronically-controlled rotating head 21 to adjust the tilt angle according to preset parameters, so as to ensure that the detection viewing field and detection angle of the multi-sensor system at the initial detection position meet imaging and detection requirements;

After reaching the detection position sequentially, the detection system uses matrix grid scanning method to acquire crops nutrition, water, growth, and pest and disease information.

The Matrix Scanning Method Described Herein is as Follows:

(1) The industrial PC 32 sends an instruction to the DSP movement controller 15 to drive the electronically-controlled rotating head 21, so as to carry out point-by-point scanning from left to right in 0-180° arc direction, with a direction perpendicular to the travel direction as the X-axis and the geometric center of the electronically-controlled rotating head 21 as the origin; at each detection position, the start point of detection in the travel direction is the initial point after the landmark sensor 36 is detected and the sliding platform stops;

(2) After the sequential detection is completed, scan the next arc grid using a step-scan method, wherein the step interval may be set according to the detection requirement and the operating efficiency requirement; specifically, the step interval may be set to a value between 10 mm and the maximum diameter of the plant crown width, to cover the entire plant crown layer; in that interval, perform arc grid scanning in the travel direction, and utilizes a laser ranging sensor 27 to acquire information of height lattice coordinate of the plant area by point scanning, to analyze crop growth information, including plant height and crown width;

(3) Whenever the scan reaches the center line of detection at 90° angle (i.e., the center line of detection superposing the geometric center line in the travel direction), utilize the binocular multi-functional imaging system 22 to acquire visible light and near-infrared binocular top-view image information of the plants;

(4) At each detection position, when the scan reaches the geometric center of the plant, utilize the infrared temperature measurement sensor 25 to acquire the crown layer temperature information of the crop, utilize the light intensity sensor 28 to acquire the environmental light intensity information at the detection position, and utilize the environmental temperature and humidity sensor 26 to acquire the environmental temperature and humidity information at the detection position.

Step 4. Comprehensive Greenhouse Crop Information Processing

Upload the comprehensive greenhouse crop information acquired in the step 3 via the information acquisition module to the industrial PC 32 for processing. Wherein, the information acquisition module uses the binocular vision images and the crop crown layer images in characteristic wave bands of nutrition and water acquired by the binocular multi.-functional imaging system 22, the lattice information of laser scanning distance acquired by the laser ranging sensor, and the infrared crown layer temperature, environmental temperature and humidity, and light intensity information as input parameters, and the input parameters are imported into the processing program in the industrial PC 32, and displayed on the touch screen 30 in real time.

Step 5. After the plant information acquisition is completed, the industrial PC 32 sends an instruction to the DSP movement controller 15 to drive the electronically-controlled rotating head 21 to rotate to the initial position and retract the lifting mechanism 19 to the initial state according to the preset journey; the sliding platform travels to the next detection position according to a preset journey; then the steps 1-5 are repeated, till the entire detection process is completed; then the sliding platform returns to the initial position.

While said examples are preferred embodiments of the present invention, the present invention is not limited to those embodiments. Any obvious improvement, replacement, or variation that can be made by those skilled in the art without departing from the spirit of the present invention shall be deemed as falling into the protection scope of the present invention.

The invention claimed is:

1. A suspended rail-type automatic cruise monitoring device for comprehensive greenhouse information, comprising a rail assembly, a travelling mechanism, a sliding platform, a multi-sensor system, and a control cabinet assembly, wherein, the rail assembly comprises a slide rail and a toothed rack that are fixed to a structural cross-beam of the greenhouse respectively;

the travelling mechanism comprises a first gear rack, a second gear rack, a deceleration motor, a gear shaft, gears, a bearing, and a photoelectric encoder, wherein the deceleration motor is connected to one end of the gear shaft by a spline; the gears are fixed on the gear shaft and mesh with a toothed rack, an other end of the gear shaft is mounted on the bearing, and the bearing is connected to the first gear rack by bolts; the first gear rack is connected to the second gear rack by bolts; top threads of the shaft of the photoelectric encoder are connected with the gear shaft to realize calculation and detection of travelling distance and position;

the sliding platform is comprised of a lifting mechanism and an electronically-controlled rotating head, comprising four sets of pulleys, a terminal limit switch, a suspension, a lifting mechanism, an electronically-controlled rotating head, a power supply of the lifting mechanism, and a DSP (Digital Signal Processor) movement controller, wherein the pulleys are fixed to the suspension and mounted in a slide channel of the slide rail, the suspension is fixed to a top of the lifting mechanism, the terminal limit switch is fixed a top of the suspension at two end positions in a forward/backward travelling direction, a bottom of the lifting mechanism is fixed to an electronically-controlled rotating head, and the DSP movement controller is used to control a forward and backward movement of an sliding platform and the up and down movement of the lifting mechanism; the power supply of the lifting mechanism supplies power to the sliding platform;

the multi-sensor system comprises a light intensity sensor, a laser ranging sensor, an infrared temperature measurement sensor, and a temperature and humidity sensor, and a binocular multi-function imaging system, wherein, a first sensor bracket and a second sensor bracket are mounted on two sides of a bottom end of the electronically-controlled rotating head respectively; the binocular multi-functional imaging system comprises a visible light multi-functional imaging system and a near-infrared multi-functional imaging system, and is fixed on the first sensor bracket, with viewing fields facing downward; a set of front optical filters for visible light is mounted on a front end of the visible light multi function imaging system, configured to acquire characteristic image information of crop nutrition; a set of front optical filters for near-infrared light is mounted on the front end of the near-infrared multi-functional imaging system, to acquire characteristic image information of water stress in the crop; wherein the visible light multi-functional imaging system and the near-infrared multi-functional imaging system are configured as a multiplexing camera for binocular vision matching, to realize three-dimensional imaging and measurement of plant height and crown width area of the crops; the infrared temperature measurement sensor, the temperature and humidity sensor, a laser ranging sensor, and a light intensity sensor are fixed on two sides of the second sensor bracket in an overlooking position, with a vertically downward detection direction;

the control cabinet assembly comprises a PC (Personal Computer) and a power supply of the PC, wherein the PC is connected with the photoelectric encoder, the DSP movement controller and the multi-sensor system.

2. The automatic cruise monitoring device according to the claim 1, wherein the slide rail is fixed below a main suspension beam, and the toothed rack is fixed below an auxiliary suspension beam.

3. The automatic cruise monitoring device according to the claim 2, wherein a cross brace is arranged between the main suspension beam and the auxiliary suspension beam.

4. The automatic cruise monitoring device according to the claim 2, wherein the seam between the two adjacent sections of the main suspension beam and the auxiliary suspension beam is fastened by connecting plates.

5. The automatic cruise monitoring device according to the claim 1, wherein the rail assembly comprises three portions: a left portion, a middle portion, and a right portion.

6. The automatic cruise monitoring device according to the claim 1, wherein the lifting mechanism is a scissor fork telescopic mechanism.

7. The automatic cruise monitoring device according to the claim 1, wherein the set of optical filters for visible light comprises 556 nm, 472 nm and 680 nm optical filters.

8. The automatic cruise monitoring device according to the claim 1, wherein the set of optical filters for near-infrared light comprises 930 nm and 1,420 nm optical filters.

9. The automatic cruise monitoring device according to the claim 1, wherein the control cabinet portion further comprises a touch display screen and a power supply of the touch display screen, wherein the touch display screen is connected with the PC.

10. The automatic cruise monitoring device according to claim 1, wherein, the PC comprises an industrial PC.

* * * * *